(12) United States Patent
Qi et al.

(10) Patent No.: US 11,020,514 B2
(45) Date of Patent: Jun. 1, 2021

(54) ABSORBABLE IRON-BASED ALLOY MEDICAL DEVICE IMPLANT

(71) Applicant: Lifetech Scientific (Shenzhen) Co., Ltd., Shenzhen (CN)

(72) Inventors: Haiping Qi, Shenzhen (CN); Wenjiao Lin, Shenzhen (CN)

(73) Assignee: Biotyx Medical (Shenzhen) Co. Ltd., Shenzhen (CN)

( * ) Notice: Subject to any disclaimer, the term of this patent is extended or adjusted under 35 U.S.C. 154(b) by 310 days.

(21) Appl. No.: 16/068,124

(22) PCT Filed: Jun. 27, 2016

(86) PCT No.: PCT/CN2016/087302
§ 371 (c)(1),
(2) Date: Jul. 4, 2018

(87) PCT Pub. No.: WO2017/117923
PCT Pub. Date: Jul. 13, 2017

(65) Prior Publication Data
US 2019/0022284 A1    Jan. 24, 2019

(30) Foreign Application Priority Data
Jan. 8, 2016    (CN) .......................... 201610013197.1

(51) Int. Cl.
*A61L 31/02*    (2006.01)
*A61L 31/08*    (2006.01)
(Continued)

(52) U.S. Cl.
CPC .......... *A61L 31/022* (2013.01); *A61L 31/086* (2013.01); *A61L 31/088* (2013.01); *A61L 31/10* (2013.01);
(Continued)

(58) Field of Classification Search
CPC .................................................... A61L 31/022
See application file for complete search history.

(56) References Cited

U.S. PATENT DOCUMENTS 4,950,453 A * 8/1990 Murray .................. C23C 22/68
                                                           204/404
5,067,990 A   11/1991 Ribitch
(Continued)

FOREIGN PATENT DOCUMENTS

CN    101851758 A  * 10/2010
CN    102228721 A    11/2011
(Continued)

OTHER PUBLICATIONS

Oka—JP S54-118349 A—ISR D#3—MT—zinc phosphate layer—1979 (Year: 1979).*
(Continued)

*Primary Examiner* — Callie E Shosho
*Assistant Examiner* — John Vincent Lawler
(74) *Attorney, Agent, or Firm* — Raymond Sun

(57) ABSTRACT

An absorbable iron-based alloy medical device implant, comprising an iron-based alloy substrate (11) and a degradable polymer (13) provided on a surface of an iron-based alloy substrate (11), and a zinc-containing protective member (12) provided on the surface of the iron-based alloy substrate (11). The zinc-containing protective member (12) is either a zinc compound or a mixture comprising the zinc compound and at least one of a phosphate-containing compound, a degradable binder, or a water-soluble binder. The weight ratio of the zinc compound in the mixture is ≥20% and <100%. The zinc-containing protective member (12) can delay corrosion of the iron-based alloy substrate (11) during an early stage of medical device implantation. The iron-based alloy substrate (11) is essentially corrosion-free during the early stage of medical device implantation, and is
(Continued)

therefore able to satisfy clinical requirements of mechanical performance during the early stage of medical device implantation.

9 Claims, 1 Drawing Sheet

(51) Int. Cl.
  *A61L 31/10* (2006.01)
  *A61L 31/14* (2006.01)
  *A61L 31/16* (2006.01)
(52) U.S. Cl.
  CPC .............. *A61L 31/148* (2013.01); *A61L 31/16* (2013.01); *A61L 2420/06* (2013.01); *A61L 2420/08* (2013.01)

(56) References Cited

U.S. PATENT DOCUMENTS

| | | | |
|---|---|---|---|
| 7,537,663 B2 * | 5/2009 | Phelps | ............... C23C 18/52 |
| | | | 148/243 |
| 2009/0177272 A1 * | 7/2009 | Abbate | ............... A61F 5/08 |
| | | | 623/1.42 |
| 2010/0331966 A1 * | 12/2010 | Borck | ............... A61L 31/022 |
| | | | 623/1.42 |
| 2016/0263287 A1 * | 9/2016 | Zhang | ............... A61L 31/146 |

FOREIGN PATENT DOCUMENTS

| | | | | |
|---|---|---|---|---|
| CN | 104587534 A | | 5/2015 | |
| CN | 104962163 A | | 10/2015 | |
| JP | 54-118349 | | 9/1979 | |
| JP | 54-118349 A | | 9/1979 | |
| JP | S54/118349 | * | 9/1979 | ............... B05D 7/14 |
| JP | S54118349 A | | 9/1979 | |

OTHER PUBLICATIONS

Cui—calcium phosphate coating on Mg alloy to modify degradation—Front.Mater.Sci.China—2008 (Year: 2008).*
Becker—Glucocorticosteroids—Anesth Prog—2013 (Year: 2013).*
Chen—biocompatability of calcium zinc phosphate coating on pure iron for biomedical apps—Mat.Sci.Eng. C—2014 (Year: 2014).*
Naisheng—CN 101851758 A—MT—corrosion inhibitor—cast iron—Zn + gluconate—2010 (Year: 2010).*
Mandavian—corrosion inhibit zinc complexes—zinc gluconate zinc acetate—Corr.Sci.—2011 (Year: 2011).*
Ashassi-Sorkhabi—Hydrodynamics_on_Corrosion_Inhibit—zinc sulfate—J.Electrochem.Soc.—2012 (Year: 2012).*
Ivusic—Corrosion inhibition—Gluconate + zinc sulfate—Tehnicki vjesnik 2014 (Year: 2014).*
Sodium gluconate _ C6H11NaO7—PubChem (Year: 2020).*
Zinc sulfate _ ZnSO4—PubChem (Year: 2020).*
Zinc gluconate _ C12H22O14Zn—PubChem (Year: 2020).*
Sodium sulfate _ Na2SO4—PubChem (Year: 2020).*
Drug Bank—zinc gluconate—2020 (Year: 2020).*
Vijayalakshmi—Coating Parameter on Corrosion Resistance Deposited Coatings_ Materials and Manufacturing Processes_ vol. 31, No. 1—2015 (Year: 2015).*
International Search Report dated Oct. 13, 2016 for corresponding PCT Application No. PCT/CN2016/087302.
Pan, Changhua Editor, "Zinc Phosphate", Encyclopedia of Small Chemical Production, Sep. 30, 1999, p. 482, lines 4-18.
Translation of Section 4 of 实用小化工生产大全 第一卷. 无机化工产品・复混肥料・农药・兽药.
Office Action dated Feb. 19, 2019 for corresponding China Application No. 201610013197.1.
Chinese Publication entitled 实用小化工生产大全 第一卷. 无机化工产品・复混肥料・农药・兽药.
Office Action dated Feb. 9, 2019 in corresponding Indian Application No. 201817029200.
Second Office Action for corresponding China Application No. 201610013197.1.
Translation for JP54-118349.

* cited by examiner

ABSORBABLE IRON-BASED ALLOY MEDICAL DEVICE IMPLANT

TECHNICAL FIELD

The present application relates to the field of absorbable medical device implants, and more particularly relates to an absorbable iron-based alloy medical device implant.

BACKGROUND ART

At present, the most frequently-used materials for an absorbable medical device implant substrate include polymers, a magnesium-based alloy and an iron-based alloy, and the most frequently used polymer is polylactic acid, which can be completely degraded and absorbed, with degradation products of carbon dioxide and water, however its mechanical property is poor. The size of a polymer-based device should be larger than the metal-based device, so that the polymer-based device has the same mechanical property as a metal-based device, which limits application of the polymer-based device. The magnesium-based alloy and the iron-based alloy have advantages of convenience in processing and molding, and high mechanical strength. However, as the magnesium-based alloy corrodes too quickly in a human body and may produce hydrogen during the corrosion, it is necessary to enlarge the size of a magnesium-based alloy device to be compatible with the mechanical property during the early stage of implantation, and because of this, the application of the magnesium-based alloy device is limited as well.

In terms of clinical application, when the absorbable medical device implant fulfills its expected use, after a diseased portion is cured and has recovered its normal shape and function (cured), so as to not cause a new biological compatibility problem, it is desirable for the device to completely degrade and to be absorbed by an organ, as quickly as possible. According to different clinical application portions of the device, the recovery period is generally considered as 1 to 6 months, and within this period of time, the device is required to keep a structural integrity and have a sufficient mechanical property. The iron-based alloy has a good biological compatibility, but due to the slow corrosion of the iron-based alloy in the body, an iron-based alloy device would require a long time to be completely corroded after the diseased portion is cured; and therefore, it is necessary to accelerate corrosion to shorten the corrosion cycle of the iron-based alloy device.

A research has shown that if the surface of the iron-based alloy is coated with a degradable polyester coating layer, its corrosion speed would be increased. Degradation of the degradable polyester coating in the body would lower the pH value of a local microenvironment near a device implantation position, thereby forming a local micro acidic environment where the iron-based alloy is corroded more quickly to generate iron salt and/or iron oxides and/or iron hydroxides which are corrosion products.

For the iron-based alloy device of a predetermined specification, the corrosion speed of the iron-based alloy, and whether the iron-based alloy is finally completely corroded or not, are determined according to the amount of use of the degradable polyester coating layer and the type and the nature of degradable polyester. Under conditions that the type and the nature of the degradable polyester have been selected and the amount of the degradable polyester, which is sufficient to completely corrode an iron-based alloy substrate, have been determined, extremely high corrosion rate or local severe corrosion of the iron-based alloy would affect the structural integrity and the mechanical property of the iron-based alloy device in the early stage of implantation (1 to 6 months, namely the above-mentioned recovery period), so it would be difficult for the device to meet the requirements for clinical application. These defects are specifically as follows: (1) a degradation product of the degradable polyester coating layer is acidic, and there are small molecular residues with a higher degradation rate in degradable polyester (for example, the standard monomer residue amount of the polylactic acid is less than 2%), that will result in faster corrosion of the iron-based substrate during the early stage of implantation; for example, after the device is implanted into a coronary artery for about 1 to 7 days, excessively fast corrosion and accumulation of the corrosion products cause incomplete endothelialization of the inner surface of the device, which increases the risk of acute thrombosis and subacute thrombosis; and (2) the heterogeneity of degradable polyester degradation easily leads to non-uniform corrosion of the iron-based alloy substrate, and local fast corrosion possibly results in breakage, so that the iron-based alloy substrate is unable to meet the requirements of structural integrity and the requisite mechanical property during the early stage. Although the excessively fast corrosion of the iron-based alloy device in the early stage of implantation can be prevented by reducing the amount of the degradable polyester coating layer, the corrosion cycle of the iron-based alloy device would be prolonged. Therefore, for an iron-based alloy device that includes the degradable polyester, under the conditions that the type and the nature of the degradable polyester and the amount ratio of the degradable polyester to the iron-based alloy have been determined, it is necessary to seek a way to reduce the early corrosion speed of the iron-based substrate in the acidic environment formed by the degradable polyester to guarantee the mechanical property of the device during the early stage of implantation.

SUMMARY OF THE INVENTION

The present application aims to provide an absorbable iron-based alloy medical device implant. In the early stage (for example within 1 to 6 months) of implantation into a body, the absorbable iron-based alloy medical device implant is corroded relatively slowly or is not totally corroded, and may meet the clinical requirement for mechanical property of the device during the early stage of implantation within this period of time.

The absorbable iron-based alloy medical device implant provided by the technical solution includes an iron-based alloy substrate, a degradable polymer disposed on the surface of the iron-based alloy substrate, and a zinc-containing protector disposed on the surface of the iron-based alloy substrate.

The zinc-containing protector may cover the entire surface of the iron-based alloy substrate, or may cover part of the surface of the iron-based alloy substrate. When the zinc-containing protector covers the entire surface of the iron-based alloy substrate, the degradable polymer covers at least part of the surface of the zinc-containing protector. When the zinc-containing protector does not completely cover the entire surface of the iron-based alloy substrate, the degradable polymer may only cover at least part of the surface of the zinc-containing protector, or also may cover a different surface of the iron-based alloy substrate together with the zinc-containing protector in a staggered manner, and also may cover at least part of the surface of the zinc-containing protector and cover at least part of non-covered regions at the same time. The zinc-containing protector may directly cover the surface of the iron-based alloy substrate, or is embedded into the iron-based alloy substrate in a block or particle manner.

The zinc-containing protector is a zinc compound, or a mixture of the zinc compound and a component selected from the group consisting of a phosphate radical-containing compound, a degradable adhesive or a water-soluble adhesive, and the weight percentage of the zinc compound in the mixture is greater than or equal to 20 percent and less than 100 percent.

The iron-based alloy substrate may be pure iron or an iron-based alloy with a carbon content less than or equal to 2.11 weight percentage, for example a product formed by nitriding and/or carburizing the pure iron.

The degradable polymer forms an acidic environment after being degraded, and an active drug may be mixed in the degradable polymer.

Compared with the prior art, the absorbable iron-based alloy medical device implant provided by the present application has the advantage that the zinc-containing protector is added. After the device is implanted into a body, the zinc-containing protector may directly play a corrosion prevention role (for example zinc phosphate), or may be dissolved and ionized or react in body fluid to generate zinc ions and then further to generate the zinc phosphate to avoid corrosion of the iron-based alloy substrate; the iron-based alloy substrate starts to be corroded quickly only after the substance having the corrosion prevention effect is nearly completely cleared away by the organ, so that the iron-based alloy substrate meets the clinical requirement for the mechanical property during the early stage of implantation. In addition, the absorbable iron-based alloy medical device implant of the present application has a smaller design size, and after being implanted, it produces fewer corrosion products and has a shorter absorption cycle.

DETAILED DESCRIPTION OF THE INVENTION

Figure 1:
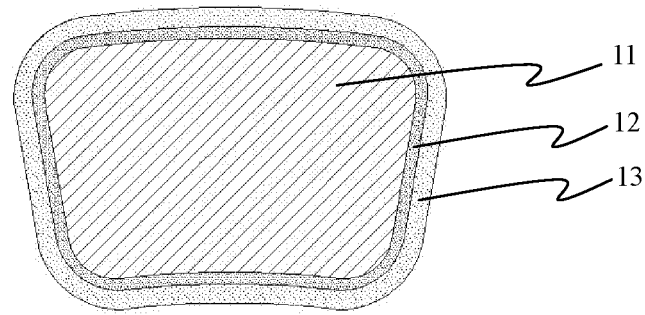
FIG. 1 is a sectional schematic diagram of an absorbable iron-based alloy medical device implant provided by one embodiment of the present application along its lengthwise direction, wherein a zinc-containing protector completely covers the entire surface of an iron-based alloy substrate.

For the purpose of facilitating understanding of the present application, a more comprehensive description will be made below to the present application with reference to relevant accompanying drawings. In the drawings, preferred embodiments of the present application are provided. However, the present application may be implemented in many different ways, but not limited to the embodiments described herein. On the contrary, the objective of providing these embodiments is to make disclosed contents of the present application more thorough and comprehensive.

Unless otherwise specified, all technical and scientific terms used in the application are the same as meanings of general understandings of technical persons skilled in the art of the present application. The terms used in the description are merely descriptive of the objectives of the specific embodiments, but not intended to limit the present application.

The main idea of the present application is that by additionally disposing a zinc-containing protector on the surface of an iron-based alloy matrix, utilizing the anti-corrosion property of the zinc-containing protector, or the property of the zinc-containing protector that it will dissolve and ionize to generate zinc ions, or that it will react to generate the zinc ions in a body fluid environment of an implantation part, and then further to generate zinc phosphate having a corrosion prevention effect to controllably slow down corrosion of the iron-based alloy substrate, the present application would achieve the effects that the iron-based alloy substrate is not corroded during the early stage (1 to 6 months) of implantation to ensure that the absorbable iron-based alloy implanted device has structural integrity and a sufficient mechanical property in the early stage, and that the corrosion cycle of the iron-based alloy substrate is not prolonged.

As the zinc-containing protector may effectively and controllably slow down the corrosion of the iron-based alloy substrate, the iron-based alloy substrate is not corroded basically within a protection period of the zinc-containing protector, and its mechanical property does not change; therefore, the absorbable iron-based alloy medical device implant of the present application only needs to ensure that its initial mechanical property before implantation can meet a clinical requirement on a lower limit during the early stage of implantation, and it is not necessary for this absorbable iron-based alloy medical device implant to have a relatively high mechanical property after the recovery period. Therefore, compared with the prior art, the absorbable iron-based alloy medical device implant of the present application has a smaller design size, and accordingly, the amount of the iron-based alloy is reduced, thereby fulfilling the objective of reducing iron corrosion products.

With reference to FIG. 1, the absorbable iron-based alloy medical device implant of the present application includes an iron-based alloy substrate 11, a zinc-containing protector 12 disposed on the iron-based alloy substrate 11, and a degradable polymer coating layer 13 disposed on the iron-based alloy substrate 11 and the zinc-containing protector 12. The iron-based alloy substrate 11 may be pure iron or an iron-based alloy with a carbon content less than or equal to 2.11 weight percent, for example a product obtained by carbonizing and/or nitriding the pure iron.

The material of the zinc-containing protector 12 may be a zinc compound, or a mixture of a zinc compound and a component selected from the group consisting of a phosphate radical-containing compound, a degradable adhesive and a water-soluble adhesive. The zinc compound may be zinc phosphate having a corrosion prevention effect, or may be zinc sulfate, zinc chloride, zinc nitrate, zinc gluconate, licorzinc, zinc lactate, zinc acetate, zinc citrate, amino acid zinc, yeast zinc and the like, which can be dissolved and ionized to generate zinc ions under a neutral environment. Or the zinc compound also may be zinc carbonate, basic zinc carbonate, zinc oxide, zinc hydroxide and the like, which can react to generate the zinc ions under an acidic environment. In the mixture of the zinc compound and the phosphate radical-containing compound or/and the adhesive, the mass percentage of the zinc compound is more than or equal to 20 percent and less than 100 percent. The phosphate radical-containing compound may be ionized to generate phosphate radical ions in the body fluid and accelerate generation of zinc phosphate to achieve a better effect of protecting an iron substrate from not being corroded; and the phosphate radical-containing compound may be phosphate or subphosphate, such as sodium phosphate, sodium dihydrogen phosphate, sodium monohydrogen phosphate, potassium phosphate, potassium dihydrogen phosphate and potassium monohydrogen phosphate, or may be other compounds capable of reacting to generate phosphate radicals, such as at least one of sodium tripolyphosphate, potassium tripolyphosphate, sodium hexametaphoshpate, potassium hexaphosphate, ammonium polyphosphate, sodium metaphosphate, potassium metaphosphate, sodium pyrophosphate and potassium pyrophosphate. The adhesive may be degraded or dissolved within a short time to expose the zinc compound after the device is implanted into a body. The adhesive may be polyethylene glycol, polyvinyl alcohol, starch, cyclodextrin or water-soluble inorganic salt. The zinc-containing protector 12 may be prepared on the iron-based alloy substrate via spray coating, dip coating, brush coating, electrostatic spinning, embedding and the like.

Figure 2:
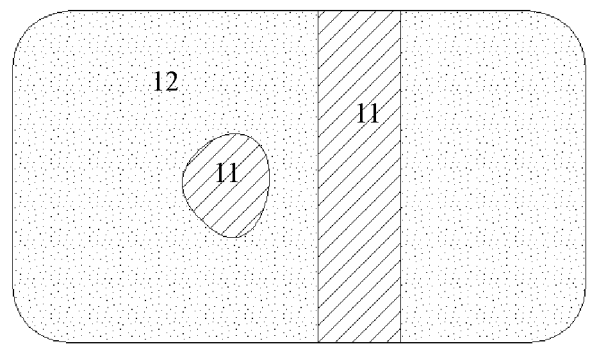
FIG. 2 is a schematic diagram of the outer surface, which is cut off and unfolded along an axial direction, of a degradable polymer-removed absorbable medical device implant provided by another embodiment of the present application, wherein a zinc-containing protector covers part of the surface of an iron-based alloy substrate.
Figure 3:
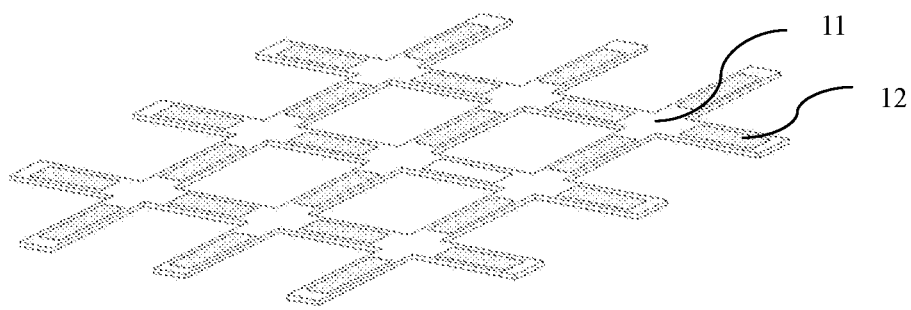
FIG. 3 is a schematic diagram of a degradable polymer-removed absorbable medical device implant provided by another embodiment of the present application, wherein a zinc-containing protector runs through an iron-based alloy substrate along a thickness direction of the substrate.

There are many relative positional relationships between the zinc-containing protector 12 and the iron-based alloy substrate 11. As one implementation mode, as shown in FIG. 1, the zinc-containing protector 12 completely and directly covers the surface of the iron-based alloy substrate 11, and the degradable polymer layer also directly and completely covers the zinc-containing protector 12. As another implementation mode, as shown in the structural diagram of a degradable polymer-removed device in FIG. 2, the zinc-containing protector 12 covers part of the surface of the iron-based alloy substrate 11 and exposes part of the surface of the iron-based alloy substrate 11. As another implementation mode, as shown in the structural diagram of a degradable polymer-removed device in FIG. 3, the zinc-containing protector 12 is embedded into the iron-based alloy substrate 11, and runs through ("run through") this substrate along a thickness direction of the iron-based alloy substrate 11, and correspondingly, the portions of the iron-based alloy substrate 11 that are not covered by the zinc-containing protector 12 are called non-covered regions. It can be understood that the zinc-containing protector 12 also may be connected with the iron-based alloy substrate 11 in other ways, for example, the zinc-containing protector 12 can be embedded into the iron-based alloy substrate 11 in a non run-through manner, and its exposed end face may be flush with the surface of the iron-based alloy substrate 11, or may protrude from or be lower than the surface of the iron-based alloy substrate 11.

When completely covering the iron-based alloy substrate 11, the zinc-containing protector 12 in contact with the body fluid may be dissolved and ionized to generate the zinc ions $Zn^{2+}$, or may react with hydrogen ions in an acidic environment generated by degradation of a degradable polymer to generate the zinc ions $Zn^{2+}$; the zinc ions $Zn^{2+}$ further react with the phosphate radicals $PO_4^{3-}$ in the body to generate insoluble zinc phosphate $Zn_3(PO_4)_2$, and reaction equations are as shown in (1) and (2):

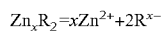
(1)

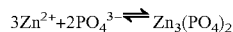
(2)

$Zn_3(PO_4)_2$ has a corrosion prevention effect, and a specific mechanism is as follows: on one hand, the zinc phosphate is dissociated to generate phosphate ions, and condensed phosphate ions react with the surface of the iron-based alloy substrate to form a complicated adhering $Fe—Zn—P_2O_5$ compound covering film to passivate the iron-based alloy substrate; on the other hand, the zinc phosphate reacts with carboxyl generated by ionization of polylactic acid to generate a complex, and this complex may react with the iron corrosion products to form a compact protective film on the surface of the iron-based alloy substrate, thereby isolating the iron-based alloy substrate from the internal environment to restrain iron corrosion. With consumption of the zinc-containing protector 12, the amount of newly generated zinc ions $Zn^{2+}$ is reduced, and the balance of the reaction (2) moves leftwards, namely the zinc phosphate is gradually dissolved, and the iron-based alloy substrate is gradually exposed; at the moment, the iron-based alloy substrate starts to be corroded slowly; and when the zinc phosphate is completely used up, the iron-based alloy substrate is completely exposed in the acidic environment and starts to be corroded quickly.

When the zinc-containing compound 12 does not completely cover the surface of the iron-based alloy substrate, the corrosion of the non-covered regions of the iron substrate is slowed down by directly diffusing the zinc phosphate to the non-covered regions or diffusing the zinc ions to the non-covered regions and then forming the zinc phosphate.

The amount (weight or volume) of the zinc-containing protector 12 is unrelated to the amount (weight or volume) of the iron-based alloy substrate 11, but is related to the type, the property (such as a degree of crystallinity, a molecular weight and a polydispersity coefficient) and the thickness (or the mass) of a degradable polymer and required time for protecting the iron-based alloy substrate 11. The amount of the zinc-containing protector 12 may be flexibly selected according to the type and the specification of the device, a clinical performance requirement of the device and an expected time length for maintaining a structural integrity and a sufficient mechanical property to adjust the time length that the zinc-containing protector 12 plays the protection role to be approximately matched with the expected time for maintaining the structural integrity and the sufficient mechanical property of the iron-based alloy substrate 11.

The degradable polymer layer includes at least one degradable polymer, which is degraded to produce an acidic degradation product, such as carboxylic acid. The degradable polymer may be selected from degradable polyester and/or degradable polyanhydride. The degradable polyester is any one of polylactic acid, polyglycolic acid, poly(lactic acid-glycolic acid), polycaprolactone, polyhydroxyalkanoate, polyacrylate, poly(ethylene succinate), poly(β-hydroxybutyrate) and polyethylene glycol adipate, or is a physical blend of at least two of the polylactic acid, the polyglycolic acid, the poly(ethylene succinate), the poly(β-hydroxybutyrate), the polycaprolactone, the polyethylene glycol adipate, a polylactic acid-glycollic acid copolymer and a polyhydroxybutyrate-pentanoate copolymer, or is any one of copolymers formed by copolymerizing at least two of monomers forming the polylactic acid, the polyglycolic acid, the poly(ethylene succinate), the poly(β-hydroxybutyrate), the polycaprolactone, the polyethylene glycol adipate, the polylactic acid-glycollic acid copolymer and the polyhydroxybutyrate-pentanoate copolymer. The degradable polyanhydride is selected from at least one of poly1,3-bis(p-carboxyphenoxy)propane-sebacic acid, poly(erucic acid dimer-sebacic acid) or poly(fumaric acid-sebacic acid), or the degradable polymer is a copolymer formed by copolymerizing at least two of monomers forming the degradable polyester and the degradable polyanhydride.

The degradable polymer coating layer may further include an active drug, and may release therapeutic drugs during degradation. For example, for a vascular stent, this active drug may inhibit excessive intimal hyperplasia after the stent is implanted and reduce the occurrence rate of restenosis in a blood vessel. The active drug may be a drug for inhibiting vascular proliferation, such as taxol, sirolimus and its derivative, or an antiplatelet drug such as cilostazol, or an antithrombotic drug such as heparin, or an anti-inflammatory reaction drug such as dexamethasone, or an anti-allergic drug such as calcium gluconate, chlortrimeton and cortisone. The active drug also may be a mixture of the above-mentioned several drugs. The anti-allergic drug may be at least one of an antihistamine type anti-allergic drug, an antileukotriens drug, a mast cell membrane stabilizer, a glucocorticoids anti-allergic drug or an immunoregulation anti-allergic drug. For example, the anti-allergic drug is selected from the goup consistng of chlortrimeton, diphenhydramine, promethazine hydrochloride, cetirizine, clarityne, mizolastine, ebastine, astemizole, terfenadine, desloratadine, fexofenadine, cyproheptadine, ketotifen, levocetirizine, meclizine, efletirizine, carebastine, azelastine, decloxizine, chlorcyclizine, amlexanox, acrivastine, azatadine, mequitazine, levocabastine, setastine, sequifenadine, deptropine, pizotifen, pyrilamine, ranitidine, emedastine, epinastine, promethazine, montelukast, zafirlukast, tomelukast, zileuton, amlexanox, ibudilast, pemirolast, doxepin, verlukast, docebenone, sodium cromoglycate, sodium hydroxypropylcromate, nedocromil sodium, tranilast, tiaramide, repirinast, bufrolin, zaprinast, tazanolast, ozagrel, repirinast, dexamethasone, methylprednisolone, hydrocortisone, triamcinolone acetonide, corticosteroids, vitamin C, calcium, coenzyme Q10 or trypsin chymotrypsin.

A preparation method for the degradable polymer layer is as follows: first dissolving the degradable polymer and the drug in an organic solvent (such as ethyl acetate or chloroform) to form a mixed solution, then coating the entire surfaces, or part of the surface, of the iron-based alloy substrate 11 having the zinc-containing protector 12 with the mixed solution, and drying the surface to form a film. Methods such as spray coating, dip coating, brush coating and electrostatic spinning may be adopted, and the spray coating is preferred.

The absorbable iron-based alloy medical device implant of the present application may be a vascular stent, an orthopedic implant, a gynecological implant, an andrology implant or a respiratory implant. A further detailed description will be made below in the present application in combination with specific embodiments by taking an iron-based alloy coronary stent as an example, but this is not intended to limit the scope of protection of the present application.

It should be noted that animal experiments in all the embodiments as follows show that under the action of the zinc-containing protector, the iron-based alloy stent experiences minimal corrosion within 1 to 6 months of the early stage of implantation. The corrosion state of the iron-based alloy stent and whether a mechanical property requirement in the early stage is met or not are determined by executing euthanasia of animals in which the stents are placed at different observation time points, such as 3 months, 6 months and 12 months, and then taking out each stent and a tissue of a portion where the stent is placed, and conducting a radial supporting strength and mass loss test on the stent and a blood vessel segment where the stent is implanted.

The radial supporting strength test is carried out with a radial supporting strength tester produced by the MSI company: taking out the stent implanted into the body of the animal and the blood vessel segment, sucking out moisture to dry the surface, and then directly carrying out the test, thus obtaining the radial supporting strengths of the stent at different time points after the stent is implanted.

One method of testing the mass loss is as follows: implanting an iron-based alloy stent (with a degradable polymer) including an iron-based alloy substrate (which is a bare stent without the degradable polymer) with a mass of M0 into an abdominal aorta of a rabbit, capturing the iron-based alloy stent implanted into the body of the animal and a tissue where the stent is implanted at a preset observation time point, then soaking the tissue and the stent in 1 mol/L sodium hydroxide solution to digest the tissue, taking the iron-based alloy stent or a fragment thereof out of the solution, putting it into a solution at a certain concentration (such as a tartaric acid solution at the concentration of 3 percent, and/or an organic solution) for ultrasonic treatment to enable a corrosion product on its surface, the residual zinc-containing protector (if any) and the polymer layer to completely fall into or be dissolved in the solution, taking the residual non-corroded iron-based alloy stent or fragment thereof out of the solution, drying and weighing it, and recording the mass as $M_r$. A mass loss rate W is represented by a percentage of a difference value of the weight loss of a corroded and cleaned stent strut to the weight of the iron-based substrate, as shown in Formula 3:

$$W=(M_r-M_0)/M_0\times 100\% \qquad (3)$$

W represents the mass loss rate $M_r$ represents the mass of the residual iron-based alloy stent substrate after corrosion $M_0$ represents the initial mass of the iron-based alloy stent substrate wherein when the mass loss rate W of the iron-based alloy substrate is less than 5 percent, it is defined that no corrosion occurs; and when the mass loss rate W of the iron-based alloy substrate is more than or equal to 90 percent, it is defined that full corrosion occurs.

Clinically, the diastolic pressure (low pressure) and the systolic pressure (high pressure) of a coronary vessel of a normal person are 60 to 120 mmHg, but the systolic pressure of a hypertension patient is up to 175 mmHg, namely 23.3 kPa. In the case of coronary artery spasm, the systolic pressure of the vessel is 400 mmHg, namely 55 kPa, A psychological stress state, a cold stimulation, a strenuous exercise, coronary atherosclerosis and a local stimulation to the coronary artery due to coronary angiogram as well as one-time heavy smoking or drinking may all induce coronary artery spasm. Thus, in order to provide an effective support for the coronary vessel, the stent should at least bear the systolic pressure of 23.3 kPa in case of pulsation of the coronary vessel, and should be equipped to bear the systolic pressure of 55 kPa in case of vasospasm.

The design target of the iron-based alloy stent provided by each embodiment as follows is to meet the following clinical requirements: within preset time (for example, within 1 month, 2 months, 3 months or other time lengths shorter than 3 months) since the date of implantation, the iron-based alloy substrate experiences minimal corrosion; and after being implanted, the iron-based alloy stent may provide effective support for 3 months; after 3 months of implantation, the radial supporting strength is more than or equal to 55 kPa; and the corrosion cycle is longer than 6 months but shorter than or equal to 24 months.

The definition of the stent of the specification 30008 in each embodiment is as follows: after the stent is expanded under the action of a nominal expansion pressure of 8 atm, the nominal diameter is 3 mm, and the nominal length is 8 mm.

It should be noted that in each embodiment as follows, a normal fluctuation of the performance of a stent product within a designed allowable range, individual differences between the animals, an insufficient density of designed sampling points, and a system error unavoidably introduced by the test methods may lead to fluctuations of monitored time points for completely no corrosion, radial strength data and full-corrosion time points of the stent within a certain range in an actual test.

Embodiment 1

An absorbable iron-based alloy stent includes a zinc-containing protector which can delay corrosion of the iron-based alloy substrate within 2 months after implantation. A preparation method of the absorbable iron-based alloy stent is as follows: selecting a nitrided iron stent of the specification 30008, which has the original radial supporting strength of 145 kPa and a mass of 4.5 to 5 mg, and coating the entire surface of the stent with suspension liquid of zinc phosphate-polyethylene glycol (with a weight-average molecular weight of 4,000)-chloroform via spray coating, drying the coated surface to obtain a zinc phosphate-polyethylene glycol coating layer with a thickness of 4 μm, wherein the volume percentage of zinc phosphate is 80 percent; and then spraying a poly-dl-lactic acid-ethyl acetate solution with a molecular weight of 200,000 to completely cover the entire surface of the zinc phosphate-polyethylene glycol coating layer, and drying the surface to obtain the absorbable iron-based alloy stent with a polylactic acid coating layer having a thickness of 12 μm. The stent is implanted into the abdominal aorta of a rabbit, and then is taken out after 2 months, and it is found that the stent is not corroded. The stent is taken out after 3 months, and it is measured that the radial supporting strength is 120 kPa, and meets a 3-month mechanical property requirement of the early stage of implantation. The stent is taken out after 12 months, and it is found that the stent is completely corroded.

Embodiment 2

An absorbable iron-based alloy stent includes a zinc-containing protector which can delay corrosion of the iron-based alloy substrate within 1 month after implantation. A preparation method of the absorbable iron-based alloy stent is as follows: selecting a nitrided iron stent of the specification 30008, which has the original radial supporting strength of 145 kPa and a mass of 4.5 to 5 mg, coating the outer surface and the side surface of the stent with a suspension solution of zinc sulfate-cyclodextrin-ethanol via spray coating, and drying the surfaces to prepare a zinc sulfate-cyclodextrin coating layer with a thickness of 12 μm, wherein the volume percentage of zinc sulfate is 90 percent; and then spraying a poly-dl-lactic acid-ethyl acetate solution with a molecular weight of 200,000 to completely cover the entire surface of the zinc sulfate-cyclodextrin coating layer and the exposed surface of the iron-based alloy stent, and drying the coated surface to obtain the absorbable iron-based alloy stent with a polylactic acid coating layer having a thickness of 8 μm. The stent is implanted into the abdominal aorta of a rabbit, and then is taken out after 1 month, and it is found that the iron-based stent is not corroded. The stent is taken out after 3 months, and it is measured that the radial supporting strength is 80 kPa, and meets a 3-month mechanical property requirement of the early stage of implantation. The stent is taken out after 12 months, and it is found that the stent is completely corroded.

Embodiment 3

An absorbable iron-based alloy stent includes a zinc-containing protector which can delay corrosion of the iron-based alloy substrate within 1 month after implantation. A preparation method of the absorbable iron-based alloy stent is as follows: selecting a nitrided iron stent of the specification 30008, which has the original radial supporting strength of 145 kPa and a mass of 4.5 to 5 mg, forming grooves, which are used for embedding zinc phosphate powder blocks, in the strut of the stent, wherein a ratio of an area exposed by all the embedded zinc phosphate powder blocks to the surface area of the iron substrate is 1:1; coating the surface of the stent with a poly-dl-lactic acid-ethyl acetate solution with a molecular weight of 200,000 via spray coating to completely cover the exposed zinc phosphate powder blocks and the exposed surface of the iron-based stent, and drying the zinc phosphate powder blocks and the surface to obtain the absorbable iron-based alloy stent with a poly-dl-lactic acid coating layer having a thickness of 6 μm. The stent is implanted into the abdominal aorta of a rabbit, and then is taken out after 1 month, and it is found that the iron-based stent is not corroded. The stent is taken out after 3 months, and it is measured that the radial supporting strength is 110 kPa. The stent is taken out after 24 months, and it is found that the stent is completely corroded.

Embodiment 4

An absorbable iron-based alloy stent includes a zinc-containing protector which can delay corrosion of the iron-based alloy substrate within 1 month after implantation. A preparation method of the absorbable iron-based alloy stent is as follows: selecting a nitrided iron stent of the specification 30008, which has the original radial supporting strength of 145 kPa and a mass of 4.5 to 5 mg, after part of the surface are protected, coating the inner surface and part of the side surface of the stent with a zinc chloride-polyethylene glycol (with a weight-average molecular weight of 4,000)-ethanol solution via dip coating, and drying the coated surface to obtain a zinc chloride-polyethylene glycol coating layer with a thickness of 12 μm, wherein the volume percentage of zinc chloride is 80 percent; and then spraying a poly-dl-lactic acid-ethyl acetate solution with a molecular weight of 200,000 to completely cover the exposed surface of the iron-based stent, and drying the coated surface to obtain the absorbable iron-based alloy stent with a polylactic acid coating layer having a thickness of 15 μm. The stent is implanted into the abdominal aorta of a rabbit, and then is taken out after 1 month, and it is found that the iron-based stent is not corroded. The stent is taken out after 3 months, and it is measured that the radial supporting strength is 80 kPa, and meets a 3-month mechanical property requirement for the early stage of implantation. The stent is taken out after 24 months of implantation, and a mass loss test shows that the stent is completely corroded.

Embodiment 5

An absorbable iron-based alloy stent includes a zinc-containing protector which can delay corrosion of the iron-based alloy substrate within 1 month after implantation. A preparation method of the absorbable iron-based alloy stent is as follows: coating the entire surface of a nitrided iron stent of the specification 30008, which has the original radial supporting strength of 145 kPa and the mass of 4.5 to 5 mg, with a zinc gluconate aqueous solution via spray coating, and drying the coated surface to prepare a zinc gluconate coating layer with a thickness of 3 μm; and then coating the surface of the zinc gluconate coating layer with a sodium tripolyphosphate solution via spraying, and then drying the coated surface to prepare a sodium tripolyphosphate coating layer with a thickness of 3 μm; coating the surface of sodium tripolyphosphate with a poly-dl-lactic acid-sirolimus-ethyl acetate solution with a molecular weight of 200,000, wherein a mass ratio of poly-dl-lactic acid to sirolimus is 4:1; and drying the coated surface to obtain the absorbable iron-based alloy stent with a polylactic acid-sirolimus coating layer having a thickness of 5 μm. The stent is implanted into the abdominal aorta of a rabbit, and then is taken out after 1 month, and it is found that the iron-based stent is not corroded. The stent is taken out after 3 months, and it is measured that the radial supporting strength is 80 kPa, and meets a 3-month mechanical property requirement for the early stage of implantation. The stent is taken out after 24 months of implantation, and a mass loss test shows that the stent is completely corroded.

Contrast 1

This contrast provides a nitrided iron bare stent (namely a stent without a degradable polymer and a zinc-containing protector) of the specification 30008, and it has the original radial strength of 145 kPa and the mass of 4.5 to 5 mg. The stent is implanted into the abdominal aorta of a rabbit. After 3 months, the stent is taken out, and a mass loss test shows that the stent is slightly corroded, and it is measured that the radial supporting strength of the stent is 140 kPa and meets a 3-month mechanical property requirement of the early stage for implantation. The stent is taken out after 24 months of the implantation, a mass loss test shows that the stent is not completely corroded, which indicates that the corrosion cycle of the nitrided iron stent without a degradable polymer layer is too long.

Contrast 2

This contrast provides an absorbable iron-based stent, and its preparation method is as follows: coating the surface of a nitrided iron stent of the specification 30008, which has the original radial strength of 145 kPa and the mass of 4.5 to 5 mg, with a poly-dl-lactic acid-ethyl acetate solution with a molecular weight of 200,000 via a spray coating manner, and drying the coated surface to obtain the absorbable iron-based alloy stent with a poly-dl-lactic acid coating layer having a thickness of 12 μm. The stent is implanted into the abdominal aorta of a rabbit, and then is taken out after 2 months, and it is found that struts of the stent are severely corroded, and multiple positions are broken. The stent is taken out after 3 months, and it is measured that the radial supporting strength of the stent is less than 55 kPa. In the sixth month after implantation, a mass loss test shows that the stent is completely corroded, which indicates that the stent corroded too quickly and may not meet the mechanical property requirement in the early stage.

Contrast 3

This contrast provides an absorbable iron-based stent, and its preparation method is as follows: coating the surfaces of a nitrided iron stent of the specification 30008, which has the original radial strength of 175 kPa and the mass of 5.5 to 6 mg, with a poly-dl-lactic acid-ethyl acetate solution with a molecular weight of 200,000 via spray coating to completely cover the entire surface of the stent, and drying the coated surface to obtain the absorbable iron-based alloy stent with a poly-dl-lactic acid coating layer having a thickness of 10 μm. The stent is implanted into an abdominal aorta of a rabbit, and then is taken out after 1 month, and it is found that the struts of the stent are corroded to a certain extent. The stent is taken out after 3 months, and it is measured that the radial supporting strength of the stent is 80 kPa and meets a 3-month mechanical property requirement for the early stage of implantation. The stent is taken out after 12 months of the implantation, and a mass loss test shows that the stent is completely corroded.

It can be seen from all the above embodiments, in the absorbable iron-based alloy stent of the present application, by the arrangement of the zinc-containing protector, the iron-based alloy substrate is slightly corroded in the early stage of implantation, and the radial supporting strength is reduced, but still meets the 3-month mechanical property requirement for the early stage of the implantation. By adjusting the amounts of the zinc-containing protector so that the time it takes for the body to consume the zinc-containing protector is approximately matched with the expected length of time that the iron-based alloy does not corrode, the adjustment of the length of time during which the stent is not corroded during the early stage of implantation is achieved. In comparison with Contrast 1, the corrosion cycles of the stents provided by Embodiments 1 to 5 are shorter. In comparison with Contrast 2, the stent provided by Embodiment 1 is slightly corroded in the early stage of implantation, and keeps a structural integrity and a sufficient mechanical support in the third month of implantation. In comparison with Contrast 3, the stent provided by Embodiment 2 adopts a smaller amount of the iron substrate on the premise of guaranteeing the same corrosion cycle and a sufficient mechanical support in the third month, so that it can be expected that a smaller number of corrosion products would be produced in the subsequent process, and the full absorption cycle is shorter.

The above embodiments only express several implementation modes of the present application, and their descriptions are relatively specific and detailed, but not intended to limit the scope of the present application thereby. It should be noted that an ordinary person skilled in the art can make various deformations and improvements without departing from the concept of the present application, and these deformations and improvements shall all fall within the scope of protection of the present application. Thus, attached claims for the scope of protection of the present application shall prevail.

The invention claimed is:

1. An absorbable iron-based alloy medical device implant, comprising an iron-based alloy substrate and a degradable polymer disposed on the surface of the iron-based alloy substrate, wherein the absorbable iron-based alloy medical device implant further comprises a zinc-containing protector disposed on the surface of the iron-based alloy substrate, wherein the zinc protector comprises a zinc sulfate-cyclodextrin coating.

2. An absorbable iron-based alloy medical device implant, comprising an iron-based alloy substrate and a degradable polymer disposed on the surface of the iron-based alloy substrate, wherein the absorbable iron-based alloy medical device implant further comprises a zinc-containing protector disposed on the surface of the iron-based alloy substrate, wherein the zinc protector comprises a zinc chloride-polyethylene glycol coating.

3. An absorbable iron-based alloy medical device implant, comprising an iron-based alloy substrate and a degradable polymer disposed on the surface of the iron-based alloy substrate, wherein the absorbable iron-based alloy medical device implant further comprises a zinc-containing protector disposed on the surface of the iron-based alloy substrate, the zinc-containing protector comprises a zinc phosphate-polyethylene glycol coating layer.

4. The absorbable iron-based alloy medical device implant according to claim 3, wherein the zinc-containing protector covers the surface of the iron-based alloy substrate, and the degradable polymer covers at least part of the surface of the zinc-containing protector.

5. The absorbable iron-based alloy medical device implant according to claim 3, wherein the degradable polymer covers at least part of the surface of the zinc-containing protector, or the zinc-containing protector and the degradable polymer cover different regions of the surface of the iron-based alloy substrate in a staggered manner, or the degradable polymer covers at least part of the surface of the zinc-containing protector, and also covers at least part of a non-covered region.

6. The absorbable iron-based alloy medical device implant according to claim 3, wherein the zinc-containing protector is in direct contact with the surface of the iron-based alloy substrate.

7. The absorbable iron-based alloy medical device implant according to claim 3, wherein the zinc-containing protector is embedded into the iron-based alloy substrate.

8. The absorbable iron-based alloy medical device implant according to claim 3, wherein the iron-based alloy substrate is pure iron or an iron-based alloy with a carbon content less than or equal to 2.11 weight percentage.

9. The absorbable iron-based alloy medical device implant according to claim 3, wherein an active drug is mixed in the degradable polymer.

* * * * *